United States Patent [19]

Fields

[11] 4,151,213

[45] Apr. 24, 1979

[54] OXIDATION CATALYST AND PROCESS

[75] Inventor: Ellis K. Fields, River Forest, Ill.

[73] Assignee: Standard Oil Company (Indiana), Chicago, Ill.

[21] Appl. No.: 761,443

[22] Filed: Jan. 21, 1977

Related U.S. Application Data

[62] Division of Ser. No. 736,564, Oct. 28, 1976, Pat. No. 4,042,531.

[51] Int. Cl.$^2$ ............................................. C07C 15/00
[52] U.S. Cl. ............................ 260/669 R; 260/668 D; 260/599; 260/586 P; 562/491; 562/493; 568/815
[58] Field of Search ....................... 260/669 R, 668 D; 252/441

[56] References Cited

U.S. PATENT DOCUMENTS

| | | | |
|---|---|---|---|
| 3,131,212 | 4/1964 | Biller | 260/669 R |
| 3,403,192 | 9/1968 | Vodekar et al. | 260/669 R |

*Primary Examiner*—Delbert E. Gantz
*Assistant Examiner*—Joseph A. Boska
*Attorney, Agent, or Firm*—William C. Clarke; Arthur G. Gilkes; William T. McClain

[57] ABSTRACT

This invention relates to a new catalyst and to a novel oxidation process. In this novel process, aromatic compounds with an alkyl group having at least one alpha hydrogen, including aromatic compounds wherein the alkyl groups are unsubstituted and substituted, are contacted in the liquid phase at reaction conditions with an oxygen-containing gas in the presence of a novel catalyst which is prepared by milling an anhydrous transition metal halide with silver nitrite, the transition metal being selected from the Groups IVb to VIII and IIb of the Periodic Table, wherein the mole ratios of metal halide to silver nitrite are in the ratio of 1:1 to 1:5.

13 Claims, No Drawings

OXIDATION CATALYST AND PROCESS

This is a division of application Ser. No. 736,564, filed Oct. 28, 1976, now U.S. Pat. No. 4,042,531.

BACKGROUND OF THE INVENTION

This invention relates to a new and useful catalyst and to a new and useful process for the oxidation of an aromatic compound in the liquid phase with an oxygen-containing gas at reaction conditions wherein the said aromatic compound has an alkyl group attached to the aromatic ring, the alkyl group containing an alpha hydrogen.

In this new and useful process, aromatic compounds with an alkyl group having at least one alpha hydrogen, including aromatic compounds wherein the alkyl groups are unsubstituted and substituted, are contacted in the liquid phase at reaction conditions with an oxygen-containing gas in the presence of a catalyst which is prepared by milling or grinding an anhydrous transition metal halide with silver nitrite, the transition metal being selected from the Groups IVb to VIII, and Ib and IIb of the Periodic Table, wherein the mole ratios of metal halide to silver nitrite are in the ratio of 1:1 to 1:5.

More particularly, the invention teaches the preparation of useful compounds through the oxidation of alkyl aromatic hydrocarbons in the liquid phase by the use of a new catalyst, including the preparation of the new catalyst.

From an industrial viewpoint, the important reactions of alkyl aromatic compounds are those involving the oxidation of methyl and ethyl groups. A number of examples can be cited. The isomers of toluic acid are bacteriostats, have use as animal feed supplements, and are used in organic syntheses to form insect repellants as well as other products. The tolyl aldehydes are useful in perfumes and in dyestuff intermediates. Ethylbenzene is reacted by oxidative dehydrogenation to form styrene monomer. Styrene is a a monomer of great industrial significance in that it is the precursor for polystyrene and is used in styrene-butadiene rubber (SBR) and in acrylonitrile-butadiene-styrene (ABS) copolymers. Cumene is oxidized to alpha-methylstyrene, a polymerization monomer especially used in polyesters.

Accordingly, the oxidation of hydrocarbons has been extensively studied and have been the subject of many publications, including patents. Two approaches have, in general, been taken in these studies of the oxidation of hydrocarbons, namely, reactions involving liquid phase reactions and those involving gaseous phase reactions.

If oxidation reactions are carried out in the gaseous phase, temperature control is an extremely important factor since all oxidations are exothermic. Precise temperature control is necessarily maintained as otherwise the oxidation continues and only the end products of the reaction are obtained, namely, carbon dioxide and water.

If the reaction is carried out in the vapor phase with a solid catalyst, the reaction, taking place at the surface of the catalyst liberates the heat of the reaction at the surface of the catalyst. The transmission of the heat to the walls of the reactor is by means of the gases, the solid catalyst, or both. Since the heat capacity of the reacting gases is typically small, an inert diluent is added often to make up for this deficiency. Steam is often used because of its high specific heat. The solid catalyst, as it is usually stationary and often a poor conductor, is of little value.

However, if the reaction can be run in the liquid phase, the higher heat capacity and better heat conductivity can aid in solving the problem of temperature control. On the other hand, it is difficult to maintain good contact between a gas and a liquid, i.e., an oxygen-containing gas, oxygen, air, etc., and a hydrocarbon, especially when the gas is not very soluble in the reacting liquid. The use of a high-speed stirrer to obtain better contact between gas and liquid phases can be required. It is also necessary that the catalyst for the liquid phase operation operate at a lower temperature than is customary for the vapor phase. This requires the development of a special type of catalyst.

A number of catalysts have been developed for the liquid phase oxidation of hydrocarbons, these catalysts being typically useful for specific applications. Among these are ammonia (U.S. Pat. No. 2,632,026 for hydroperoxides), alkali and alkaline-earth metal formates, oxalates and benzoates (U.S. Pat. No. 2,681,937—alkyl aromatic hydroperoxides), sodium carbonate (U.S. Pat. No. 2,681,936—cumene hydroperoxide), the oxidative product of polycondensation of 2,4-diamino-5-phenylazotoluene (U.S.S.R. No. 176,874—cumene hydroperoxide and dimethylphenylcarbinol), a cobaltous acetate, i.e. $Co(OAc)_2.4H_2O$ (Belg. No. 646,849—phthalic acids), calcium hydroxide (U.S. Pat. No. 2,447,400—acetophenone and dimethylphenylcarbinol), manganese dioxide and manganese p-toluate (Senseman et al, IEC, 24 1184 (1932)—acetophenone), manganese acetate (King et al, IEC, 21 1227 (1929)—acetophenone).

While a large number of catalysts and procedures have been developed and disclosed for liquid phase oxidation of alkylbenzenes, the catalysts and processes are typically specific for particular products. Therefore there is a continuing need for new catalysts and new procedures with specific application in the obtaining of economically valuable products, the said catalysts being such as to permit their use in liquid phase oxidations of hydrocarbons.

SUMMARY OF THE INVENTION

Catalyst and process for oxidation of alkyl aromatic compounds, the alkyl group being attached directly to the aromatic ring and having at least one alpha hydrogen, wherein the alkyl aromatic compound is contacted in the liquid phase at reaction conditions with an oxygen-containing gas in the presence of a novel catalyst prepared by milling an anhydrous transition metal halide with silver nitrite, the transition metal being selected from the Groups IVb to VIII, and Ib and IIb of the Periodic Table, the mole ratios of said metal halide to said silver nitrite being in the ratio of 1:1 to 1:5.

DETAILED DESCRIPTION OF THE INVENTION

This invention relates to a catalyst and an oxidation process for alkyl aromatic compounds wherein the said aromatic compound is contacted in the liquid phase at reaction conditions with an oxygen-containing gas such as molecular oxygen or air in the presence of a novel catalyst comprising a milled reaction product of an anhydrous transition metal halide with silver nitrite.

The new catalyst of this invention relates to a solid catalyst which is dispersed throughout the liquid phase of the reacting hydrocarbon which is commingled with an oxygen-containing gas such as molecular oxygen or air, the dispersion of the solid catalyst being maintained by a stirring mechanism.

The proportion of catalyst employed can vary within fairly wide limits depending to some extent upon the operating conditions chosen, the optimum amount being determinable by a single preliminary test. It is usually advantageous when large quantities of catalyst are used to introduce the catalyst in portions during the course of the reaction.

For purposes of this invention, the alkyl aromatic hydrocarbons can be represented by $R\text{-}X_n$ where R is a radical of a compound of aromatic character, the radical R having 6 to 14 carbon atoms such as phenyl, biphenyl, naphthyl, anthranyl or phenanthryl radicals, X is an alkyl moiety, straight chain or branched, containing 1 to 20 carbon atoms such as methyl, ethyl, isopropyl, n-propyl, n-butyl or isobutyl, but not tert-alkyl such as tert-butyl, and n is an integer from 1 to 4. It is essential that the alkyl moiety contain at least 1 alpha hydrogen. R can be substituted with individually selected substituents such as cyano; carboxy, and ester groups such as carbomethoxy; nitro; and halogens (fluorine, chlorine, bromine and iodine). The number of substituents apart from hydrogen and X can be from 1 to 5. Hydrogen moieties fulfill the remaining unsubstituted positions of the radical R.

For purposes of this invention, the term "oxidation" is defined as the loss or transfer of electrons with the substance gaining the electrons constituting the oxidizing agent. "Oxidative dehydrogenation" is defined as a form of oxidation in which the loss of electrons is accompanied by the removal of hydrogen.

The term "transition metal halide" is defined as being the halide of the metals found in the Groups IVb to VIII, and Ib and IIb of the Periodic Table of the Elements found in the 56th Edition of the Handbook of Chemistry and Physics published by The Chemical Rubber Company. Included are those metals in periodic sequence from titanium to zinc, namely titanium, vanadium, manganese, iron, cobalt, nickel, copper, zinc and, additionally, tungsten and thallium. The bromide of these metal halides is preferable because the bromide demonstrates the best reaction with silver nitrite; there being no immediate reaction of silver nitrite with the fluoride salts of these metals and only a slight reaction with chloride salt.

In general, in the oxidation process of this invention, the alkyl aromatic hydrocarbon is contacted in the liquid phase with an oxidizing agent selected from the group consisting of an oxygen-containing gas which can be in the form of molecular oxygen or an oxygen-containing gas such as air, in the presence of a catalyst prepared by milling an anhydrous transition metal bromide with silver nitrite, at a reaction temperature within the range of from 100° to 250° C. under a pressure of from 1 to 100 atmospheres for periods of from 1 to 100 hours. If the oxidizing agent is molecular oxygen, oxygen flow rate is within the range from about 200 to 5000 cc/minute. A high speed stirrer is utilized to maintain contact between the alkyl aromatic hydrocarbon, the catalyst and the oxygen-containing gas. Preferred reaction conditions are 110° to 180° C. at 1 to 10 atmospheres for 2 to 10 hours. A maximum temperature of 180° C. is preferred because of possible catalyst breakdown at temperatures over 180° C. A minimum temperature of 110° C. is preferred because oxidation becomes unacceptably slow below 110° C. Range of catalyst addition is 0.1 to 10 (wgt)% of the alkyl aromatic hydrocarbon. The catalyst can be recovered and reused after filtering from the said aromatic hydrocarbon.

In the practice of the invention, the oxygen-containing gas such as molecular oxygen or air can be introduced by means of a hollow vibrating stirrer into the reaction mixture at a flow rate such that the gas is dispersed throughout the mixture in fine bubbles through the action of the stirrer. The speed of the stirrer is maintained at such a rate, about 3600 vibrations per minute, so as to agitate the mixture vigorously and to keep the heavier catalyst in suspension. The reaction is continued until standard analytical data, such as refractive index, indicate the conversion to oxidized products of the original aromatic hydrocarbon from about 15% to about 65%. The reaction mixture can then be treated in accordance with known techniques to obtain a product containing preponderant amounts of the oxidized products.

In general, the reaction between the halide and silver nitrite is carried out by reacting, during milling or grinding, 1 mole of halide to 1 mole of silver nitrite to 1 mole of halide to 5 moles of silver nitrite, preferably 1 mole of metal halide to 2 moles of silver nitrite as dry, anhydrous materials. The silver nitrite is preferably freshly prepared. The milling period is preferably short, not greater than 25 seconds as decomposition can occur of the milled metal halide-silver nitrite product with excessive evolution of $N_2O_4$. In some cases, the reaction of the metal halide and silver nitrite can be excessively exothermic. In such instances, a mixture of the two materials is preferably stirred gently and cautiously together before milling together to avoid a vigorous reaction in the milling process.

The milling procedure utilized a Moulinex solids mill of 1000 to 10,000 RPM with provision for cold air circulation to reduce milling temperatures. Preferred RPM is approximately 2000 RPM. A ball mill with balls of an inert material such as porcelain and other ceramic materials can also be used. Liquid cooling can be used with an enclosed ball mill. Reaction temperature during milling is accordingly kept within the range of from 0° to 60° C. to prevent a violently exothermic reaction. Preferred reaction temperature during milling is within the range of 20° to 30° C.

In order to facilitate a clear understanding of the invention, i.e., the novel oxidation process in the presence of a catalyst, the following specific embodiments are described in detail. It should be understood, however, that the detailed expositions of the application of the invention, while indicating preferred embodiments, are given by way of illustration only since various changes and modifications within the spirit and scope of the invention will become apparent to those skilled in the art from this detailed description.

Example I illustrates the preparation of the catalyst.

EXAMPLE I

A mixture of 11.16 g (0.05 mole) of anhydrous cupric bromide and 15.4 g (0.10 mole) of dry, freshly-prepared silver nitrite was milled together in a high-speed Moulinex powder mill for 10 seconds at 22° C. Milling speed was 2000 RPM. The temperature rose to 45° C.; all the intense black color of cupric bromide changed to a light green, and a small amount of $N_2O_4$ was given off. The resulting green product weighed 26.47 g; it was stored in the dark and used as a catalyst in the following examples.

EXAMPLE II

Using the catalyst of Example I, oxidation of o-xylene gave a high yield of oxidized products.

A mixture of 250 ml (221 g) of o-xylene and 5 g of catalyst of Example I was refluxed and stirred in a Vibro-mixer (model E-1, A. G. fur Chemie-Apparatebau, Mannedorf ZH, Switzerland) with oxygen flowing into the mixture through a hollow stirrer at 500 cc/min. for 5.5 hours. Stirrer speed was 3600 vibrations per minute. Reaction temperature was 144° C. The mixture was cooled to 0° C. and filtered; the filtrate was distilled to recover 150 g of o-xylene and obtain a residue of 58.8 g that consisted of

| Product | Wt. % |
|---|---|
| o-methylbenzyl alcohol | 5.6 |
| o-methyl benzaldehyde | 7.6 |
| o-toluic acid | 51.0 |
| phthalide | 2.3 |
| 2,2',3'-trimethyl diphenylmethane | 30.8 |
| 2,2',3'-dimethyl carboxydiphenylmethane | 2.7 |

EXAMPLE III

A large proportion of m-methylbenzaldehyde results from oxidation of m-xylene using the process and catalyst of my invention.

The procedure of Example II was followed, using 250 ml (216 g) m-xylene. Reaction temperature was 139° C. The filtrate was distilled to recover 212 g of m-xylene and obtain a residue of 1.11 g that consisted of:

| Product | Wt. % |
|---|---|
| m-methylbenzyl alcohol | 5.4 |
| m-methylbenzaldehyde | 41.6 |
| m-toluic acid | 4.3 |
| 4-bromo-m-xylene | 33.7 |
| 2,4,3'-trimethyl diphenylmethane | 15.0 |

EXAMPLE IV

An increased yield was obtained from m-xylene using m-toluic acid and 5 g of catalyst of Example I.

The procedure of Example II was followed using 250 ml of m-xylene plus 1 g of m-toluic acid. Reaction temperature was 139° C. The filtrate was distilled to recover 205 g of m-xylene and obtain a residue of 7.8 g that consisted of:

| Product | Wt. % |
|---|---|
| m-methylbenzyl alcohol | 1.2 |
| m-methylbenzaldehyde | 45.1 |
| m-toluic acid | 37.8 |
| 2,4,3'-trimethyl diphenylmethane | 3.3 |
| dimethyl hydroxymethyl diphenylmethane | 4.5 |
| dimethyl diphenylmethane carboxylic acid | 6.7 |
| methyl carboxydiphenylmethane carboxaldehyde | 1.4 |

EXAMPLE V p-Xylene was oxidized to yield considerable amounts of p-methyl-benzyl alcohol and p-methylbenzaldehyde.

The procedure of Example II was followed using 250 ml (215.2 g) of p-xylene. Reaction temperature was 138° C. The filtrate was distilled to recover 187 g of p-xylene and obtain a residue of 21.8 g that consisted of:

| Product | Wt. % |
|---|---|
| p-methylbenzyl alcohol | 16.7 |
| p-methylbenzaldehyde | 24.5 |
| p-toluic acid | 44.9 |
| 2,4,4'-trimethyl diphenylmethane | 3.5 |
| 5,4'-dimethyl diphenylmethane-2-carboxylic acid | 8.6 |
| 2-carboxy-5-methyl diphenylmethane-4'-carboxyaldehyde | 1.8 |

EXAMPLE VI

Almost complete oxidative dehydrogenation of ethylbenzene to styrene was achieved with the catalyst of Example I.

The procedure of Example II was followed using 250 ml (216.8 g) of ethylbenzene. Reaction temperature was 136° C. The filtrate was distilled to recover 118 g of ethylbenzene and obtain a residue of 80.6 g that consisted of:

| Product | Wt. % |
|---|---|
| styrene | 81 |
| acetophenone | 8.2 |
| 1-phenylethanol | 6.5 |
| benzalacetophenone | 4.3 |

EXAMPLE VII

Almost complete oxidation of cumene to α-methylstyrene was obtained with the catalyst of Example I.

The procedure of Example II was followed, using 250 ml (215.5 g) of cumene. Reaction temperature was 152° C. The filtrate was distilled to recover 101 g of cumene and obtain a residue of 109.2 that consisted of:

| Product | Wt. % |
|---|---|
| α-methylstyrene | 95.2 |
| cumyl-alcohol | 2.3 |
| αmethylstyrene epoxide | 1.3 |
| benzalacetophenone | 1.2 |

EXAMPLE VIII

Methyl-p-toluate oxidized to bifunctional monomers, dimethyl diphenylmethane-4,4'-dicarboxylate and dimethylbenzoin-4,4'-dicarboxylate, both monomers for polyesters.

The procedure of Example II was followed, using 250 ml (267 g) of methyl-p-toluate. Reaction temperature was 150° C. The filtrate was distilled to recover 247 g of methyl p-toluate and obtain a residue of 17.9 g. that consisted of:

| Product | Wt. % |
|---|---|
| p-toluic acid | 9.4 |
| monomethyl terephthalate | 4.9 |
| dimethyl diphenylmethane-4,4'-dicarboxylate | 22.1 |
| dimethyl 2-hydroxymethyl-diphenylmethane-5,5'-dicarboxylate | 14.4 |
| dimethyl benzoin-4,4'-dicarboxylate | 44.7 |
| trimethyl diphenylcarbinol-2,5,4'-tricarboxylate | 4.5 |

EXAMPLE IX

To demonstrate the effectiveness of my new process and catalyst as compared to that of the individual components, I followed the procedure of Example II using 250 ml of p-xylene with each of 3 different catalysts. The process and catalyst of my invention clearly are superior in giving twice as high a yield of products and a different distribution of products compared with the other catalysts.

Catalyst 1.

5 g of my novel catalyst, Example I

Catalyst 2.

7.7 g of silver nitrite plus 5.58 g of anhydrous cupric bromide added separately to stirred p-xylene, then 1 ml of tert-butyl peroxide to initiate oxidation radical chains.

Catalyst 3.

5 g of anhydrous cupric bromide plus 1 ml of tertbutyl peroxide as an initiator.

Yields of products are shown in the table.

|  | Catalyst | | |
| --- | --- | --- | --- |
|  | 1. | 2. | 3. |
| Reaction Temperature | 138° C. | 138° C. | 138° C. |
| Wt. of products, g. | 21.8 | 9.4 | 10.6 |
| Product | Wt. % | Wt. % | Wt. % |
| p-methylbenzyl alcohol | 16.7 | 1.6 | — |
| p-methylbenzaldehyde | 24.5 | 25.1 | 9.0 |
| p-toluic acid | 44.9 | 11.5 | 2.7 |
| 2,5,4'-trimethyl diphenylmethane (dehydrodimer) | 3.5 | 35.8 | 72.4 |
| 5,4'-dimethyl diphenylmethane-2-carboxylic acid | 8.6 | 10.3 | — |
| bromo-p-xylene | — | 13.8 | 5.1 |
| dehydrotrimer | — | 0.6 | 9.8 |
| dehydrotetramer | — | — | 1.0 |
| bromodehydrodimer | — | 1.3 | — |
| 2-carboxy-5-methyl diphenylmethane-4'-carboxaldehyde | 1.8 | — | — |

Under the same conditions, p-xylene with 1 ml tert-butyl peroxide alone gave 1.9 g of product that consisted of:

| Product | Wt. % |
| --- | --- |
| p-toluic acid | 35.5 |
| p-methylbenzyl alcohol | 32.9 |
| p-methylbenzaldehyde | 17.1 |
| p-methylbenzyl-p-toluate | 14.5 | p-Xylene with no catalyst at all gave 0.7 g of product that was not analyzed.

The following Examples X-XVII illustrate the preparation of the catalysts of silver nitrite and halides of other transition metals.

EXAMPLE X

In the procedure of Example I, a mixture of 6.42 g (30 mmole) of anhydrous manganese bromide and 9.23 g (60 mmole) of silver nitrite was milled together in a high speed Moulinex powder mill for 15 seconds. Milling speed was 2000 RPM. Temperature was 25° C. The pink color of $MnBr_2$ disappeared. The resulting product, a yellow-white powder, weighed 15.4 g.

EXAMPLE XI

A mixture of 6.56 g (30 mmole) of anhydrous cobaltous bromide and 9.23 g (60 mmole) of silver nitrite was milled together for 15 seconds. Milling speed was 2000 RPM. Temperature was 25° C. The deep green color of $CoBr_2$ became that of the product, light grey-green, 15.6 g.

EXAMPLE XII

A mixture of 5.83 g (20 mmoles) of anhydrous chromium tribromide and 9.2 g (60 mmole) of silver nitrite was milled together for 15 seconds. Milling speed was 2000 RPM. Temperature was 25° C. The deep black color of $CrBr_3$ became that of the product, grey, 15 g.

EXAMPLE XIII

A mixture of 5.91 g (20 mmole) of anhydrous ferric bromide and 9.2 g (60 mmole) of silver nitrite was milled together for 10 seconds. Milling speed was 2000 RPM. Temperature was 30° C. The black color of $FeBr_3$ became that of the product, light grey, 14.8 g.

EXAMPLE XIV

A mixture of 6.54 g (30 mmole) of anhydrous nickel bromide and 9.2 g (60 mmole) of silver nitrite was milled together for 15 seconds. Milling speed was 2000 RPM. Temperature was 30° C. The deep brown color of $NiBr_2$ became that of the product, pale orange, 15.6 g.

EXAMPLE XV

A mixture of 5.81 g (20 mmole) of anhydrous vanadium bromide and 9.2 g (60 mmole) of silver nitrite was milled together for 10 seconds. Milling speed was 2000 RPM. Temperature was 45° C. The reaction was vigorous, evolved much heat and some $NO_2$. The black color of $VBr_3$ became that of the product, grey, 14.4 g.

EXAMPLE XVI

A mixture of 17.04 g (60 mmole) of anhydrous thallium (I) bromide and 9.2 g (60 mmole) of silver nitrite was milled together for 10 seconds. Milling speed was 2000 RPM. Temperature was 20° C. The light yellow TlBr went to orange, then green of the product, 26.2 g. Very dense powder.

EXAMPLE XVII

A mixture of 5.83 g (10 mmole) of anhydrous tungsten pentabromide and 7.7 g (50 mmole) of silver nitrite was stirred together cautiously. The mixture caught fire and evolved $NO_2$. After the vigorous reaction subsided, the mixture was milled together for 5 seconds to give 11.4 g of grey powder. Milling speed was 2000 RPM. Temperature was 30° C.

EXAMPLE XVIII

In the procedure of Example II, mixtures of 250 ml (221 g) of o-xylene and 5 g of products of Examples X-XVII separately were refluxed and stirred in a Vibromixer with oxygen flowing into the mixture at 500 cc/min. for 5.5 hours. The mixtures were cooled and filtered; the filtrates were distilled to recover unreacted o-xylene and obtain residues that were analyzed by gas chromatography and mass spectrometry. For a comparison, the results obtained in Example II are included which were obtained with the catalyst from anhydrous cupric bromide and silver nitrite of Example I. The results are shown in Table II.

TABLE

Yields of Products From Oxidation of o-Xylene in the Liquid Phase

| | Catalysts of Examples I and X–XVII Yields, in g. | | | | | | | | |
|---|---|---|---|---|---|---|---|---|---|
| Example | I Cu-Ag, | X Mn-Ag, | XI Co-Ag, | XII Cr-Ag, | XIII Fe-Ag, | XIV Ni-Ag, | XV V-Ag, | XVI Tl-Ag, | XVII W-Ag, |
| Reaction Temp. °C., 144° C. | | | | | | | | | |
| Products, g. | | | | | | | | | |
| o-Methylbenzyl alcohol | 3.3 | 1.5 | 4.2 | 1.9 | 1.2 | 1.0 | 1.6 | 5.3 | 5.4 |
| o-Methylbenzaldehyde | 4.5 | 0.4 | 2.1 | 2.0 | 0.5 | 1.7 | 1.3 | 1.9 | 2.7 |
| o-Toluic Acid | 30.0 | 0.1 | 2.5 | 4.2 | 0.1 | 3.1 | 8.8 | 6.4 | 2.5 |
| Phthalide | 1.4 | — | 0.2 | 0.1 | — | 0.1 | 0.2 | 0.2 | 0.2 |
| 2,2',3'-Trimethyl diphenylmethane | 18.1 | 1.3 | 1.0 | 1.4 | 0.5 | 1.0 | 1.4 | 3.9 | 3.3 |
| 2,2',3'-Dimethyl carboxydiphenyl-methane | 1.6 | — | 0.1 | — | — | — | 0.1 | 0.1 | 0.2 |

EXAMPLE XIX

The procedure of Example XVIII was followed using 250 ml (216.8 g) of ethylbenzene. The products are shown in Table III.

TABLE III

Yields of Products from Liquid-Phase Oxidation of Ethylbenzene

| | Catalysts of Examples I and X–XVI Yields, in g. | | | | | | | | |
|---|---|---|---|---|---|---|---|---|---|
| Example | I Cu-Ag, | X Mn-Ag, | XI Co-Ag, | XII Cr-Ag, | XIII Fe-Ag, | XIV Ni-Ag, | XV V-Ag, | XVI Tl-Ag, | XVII W-Ag, |
| Reaction Temp. °C., 136° C. | | | | | | | | | |
| Products, g. | | | | | | | | | |
| Styrene | 65.3 | 7.1 | 15.5 | 6.5 | 4.5 | 4.6 | 2.1 | 0.5 | 0.8 |
| Acetophenone | 6.6 | 17.0 | 40.6 | 11.3 | 0.5 | 0.8 | | | |
| 1-Phenylethanol | 5.2 | 8.1 | 7.0 | 11.5 | 2.5 | 5.4 | 3.4 | 1.0 | 0.5 |
| Benzalacetophenone | 3.5 | — | — | — | — | — | — | — | — |

From the data of Examples XVIII and XIX in Tables II and III, the catalyst prepared by reacting anhydrous cupric bromide with silver nitrite is more active in catalyzing liquid-phase oxidations than the other transition-metal catalysts. However, all products of anhydrous bromides with silver nitrite have some catalytic activity; in particular, the reaction product of tungsten pentabromide with silver nitrite, Example XVII, gave 1.7 g of phenol from ethylbenzene in addition to the products shown in Table III.

I claim:

1. A process for oxidation of alkyl aromatic compounds, the alkyl moiety being attached directly to the aromatic ring and having at least one alpha hydrogen wherein the said alkyl aromatic compound is contacted in the liquid phase with an oxygen-containing gas in the presence of an oxidation catalyst consisting essentially of a milled reaction product of an anhydrous transition metal halide with silver nitrite wherein the said transition metal is selected from the group consisting of copper, manganese, cobalt, chromium, iron, nickel, vanadium, thallium and tungsten, the mole ratio of said metal halide to said silver nitrite before said milling being in the ratio of 1:1 to 1:5, at a temperature within the range of from about 100° to 250° C., at a pressure within the range of 1 to 100 atmospheres and an oxygen flow rate within the range from about 200 to 5000 cc/minute.

2. The process of claim 1 wherein the said transition metal is copper.

3. The process of claim 1 wherein the said transition metal is tungsten.

4. The process of claim 1 wherein the said oxygen-containing gas is molecular oxygen.

5. The process of claim 1 wherein the said oxygen-containing gas is air.

6. The process of claim 1 wherein the said temperature is within the range from about 110° to 180° C.

7. The process of claim 1 wherein the said pressure is within the range from about 1 to 10 atmospheres.

8. The process of claim 1 wherein the mole ratio of metal halide to silver nitrite of said catalyst is 1:2.

9. The process of claim 1 wherein the metal halide of said catalyst is cupric bromide.

10. The process of claim 1 wherein the said alkyl aromatic compound is ethylbenzene.

11. The process of claim 1 wherein the said alkyl aromatic compound is cumene.

12. The process of claim 9 wherein the metal halide of said catalyst is tungsten pentabromide.

13. The process of claim 9 wherein the said alkyl aromatic compound is ethylbenzene.

* * * * *

UNITED STATES PATENT OFFICE
CERTIFICATE OF CORRECTION

Patent No. 4,151,213          Dated April 24, 1979

Inventor(s) Ellis K. Fields

It is certified that error appears in the above-identified patent and that said Letters Patent are hereby corrected as shown below:

| Patent Column | Line | |
|---|---|---|
| Abstract | 10 | "Groups IVb to VIII and IIb" should be --Groups IVb to VIII and Ib and IIb-- |
| 1 | 39 | "is a a" should be --is a-- |
| 6 | 8 | "2,4,4'-trimethyl diphenylmethane" should be --2,5,4'-trimethyl diphenylmethane-- |
| 6 | 38 | "109.2" should be --109.2g-- |
| 9 | 1 | "TABLE" should be --TABLE II-- |
| 9 | 27 | "X-XVI" should be --X-XVII-- |

UNITED STATES PATENT OFFICE
CERTIFICATE OF CORRECTION

Patent No. 4,151,213  Dated April 24, 1979

Inventor(s) Ellis K. Fields

It is certified that error appears in the above-identified patent and that said Letters Patent are hereby corrected as shown below:

| Patent Column | Line | |
|---|---|---|
| 9 | 35 | entries for "Acetophenone" in Table III are wrong for Exs. XIII - XVII - should be |

| XIII | XIV | XV | XVI | XVII |
|---|---|---|---|---|
| 5.1 | 61.0 | 11.3 | 0.5 | 0.8 |

| | | |
|---|---|---|
| 10 | 57 | "Claim 9" should be --Claim 1-- |
| 10 | 59 | "Claim 9" should be --Claim 1-- |

Signed and Sealed this

Nineteenth Day of August 1980

[SEAL]

Attest:

SIDNEY A. DIAMOND

Attesting Officer    Commissioner of Patents and Trademarks